United States Patent
Burchill et al.

(10) Patent No.: US 10,539,290 B2
(45) Date of Patent: Jan. 21, 2020

(54) OPTICAL LIGHT DIFFUSER AND METHOD FOR MEASUREMENT THEREOF

(71) Applicants: Michael T. Burchill, Langhorne, PA (US); Steven W. Gaskey, Ambler, PA (US); Robert A. Wanat, Langhorne, PA (US); Jiaxin Ge, Lower Providence, PA (US); Mark A. Aubart, West Chester, PA (US); Arkema France, Colombes (FR)

(72) Inventors: Michael T. Burchill, Langhorne, PA (US); Steven W. Gaskey, Ambler, PA (US); Robert A. Wanat, Langhorne, PA (US); Jiaxin Ge, Lower Providence, PA (US); Mark A. Aubart, West Chester, PA (US)

(73) Assignee: Arkema France, Cololmbes (FR)

( * ) Notice: Subject to any disclaimer, the term of this patent is extended or adjusted under 35 U.S.C. 154(b) by 0 days.

(21) Appl. No.: 14/431,466

(22) PCT Filed: Sep. 27, 2013

(86) PCT No.: PCT/US2013/062068
§ 371 (c)(1),
(2) Date: Mar. 26, 2015

(87) PCT Pub. No.: WO2014/055330
PCT Pub. Date: Apr. 10, 2014

(65) Prior Publication Data
US 2015/0267891 A1    Sep. 24, 2015

Related U.S. Application Data

(60) Provisional application No. 61/708,216, filed on Oct. 1, 2012.

(51) Int. Cl.
*F21V 3/06*    (2018.01)
*G02B 5/02*    (2006.01)
(Continued)

(52) U.S. Cl.
CPC ............ *F21V 3/0625* (2018.02); *G01N 21/59* (2013.01); *G02B 5/0242* (2013.01); *F21V 3/049* (2013.01);
(Continued)

(58) Field of Classification Search
CPC ...... F21V 3/0445; F21V 3/0625; F21V 3/049; F21V 5/00; F21K 9/50; G01N 21/59;
(Continued)

(56) References Cited

U.S. PATENT DOCUMENTS 5,237,004 A *   8/1993   Wu ..................... C08F 265/04
                                             525/228
5,856,378 A *   1/1999   Ring ..................... C08J 3/203
                                             428/407
(Continued)

FOREIGN PATENT DOCUMENTS

WO    WO 2006/100126    9/2006

*Primary Examiner* — Anh T Mai
*Assistant Examiner* — Fatima N Farokhrooz
(74) *Attorney, Agent, or Firm* — Thomas F. Roland

(57) ABSTRACT

The invention relates to optical light diffusers for use with point light sources, such as LED lighting. The optical diffusers achieve an optimum balance of light transmission and hiding power. The optical light diffuser is a transparent plastic matrix, such as Plexiglas® resin from Arkema Inc., having organic particles dispersed within the matrix. The particles are crosslinked beads having specific particle sizes and loading. Different beads can be combined to provide added properties such as a textured surface, and to optimize hiding power and light transmission. The invention also relates to a luminous device containing at least one light-emitting diode and a cover made of the optical light diffuser. The invention further relates to a method for assessing hiding power.

14 Claims, 2 Drawing Sheets

(51) Int. Cl.
*G01N 21/59* (2006.01)
*F21V 3/04* (2018.01)
*F21Y 115/10* (2016.01)

(52) U.S. Cl.
CPC ..... *F21Y 2115/10* (2016.08); *G01N 2201/062* (2013.01); *G01N 2201/0634* (2013.01)

(58) Field of Classification Search
CPC ...... G01N 2201/062; G01N 2201/0634; F21Y 2101/02; F21Y 2115/10; G02B 5/0242; Y10T 428/24479
See application file for complete search history.

(56) References Cited

U.S. PATENT DOCUMENTS

| | | | |
|---|---|---|---|
| 6,360,562 B1 * | 3/2002 | Kodas | A61K 6/0276 |
| | | | 257/E21.304 |
| 6,780,501 B2 | 8/2004 | Bruneau et al. | |
| 6,979,704 B1 * | 12/2005 | Mayer | B82Y 30/00 |
| | | | 523/220 |
| 7,547,736 B2 | 6/2009 | Yang et al. | |
| 7,829,626 B2 * | 11/2010 | Chiou | C09D 7/69 |
| | | | 524/522 |
| 7,980,734 B2 | 7/2011 | Hahn et al. | |
| 8,163,827 B2 | 4/2012 | Garcia-Leiner et al. | |
| 8,227,073 B2 | 7/2012 | Fujii et al. | |
| 2003/0002158 A1 | 1/2003 | Masaki et al. | |
| 2003/0218192 A1 * | 11/2003 | Reilly | B32B 5/16 |
| | | | 257/200 |
| 2004/0202822 A1 * | 10/2004 | Bourdelais | B32B 7/02 |
| | | | 428/143 |
| 2006/0160944 A1 * | 7/2006 | Yang | B29C 47/0004 |
| | | | 524/513 |
| 2006/0240200 A1 | 10/2006 | Parusel et al. | |
| 2007/0110948 A1 | 5/2007 | Lacock et al. | |
| 2008/0080055 A1 | 4/2008 | Lightfoot et al. | |
| 2008/0219028 A1 * | 9/2008 | Brewer | G02B 5/0221 |
| | | | 362/627 |
| 2009/0284970 A1 * | 11/2009 | Graf | G02B 5/0231 |
| | | | 362/247 |
| 2009/0316261 A1 * | 12/2009 | Garcia-Leiner | B32B 27/04 |
| | | | 359/453 |
| 2010/0067258 A1 | 3/2010 | Hahn et al. | |
| 2010/0079701 A1 | 4/2010 | Murayama et al. | |
| 2011/0213069 A1 * | 9/2011 | Kanazawa | C09D 7/69 |
| | | | 524/520 |
| 2011/0255167 A1 | 10/2011 | Merrill et al. | |
| 2011/0315189 A1 | 12/2011 | Ge et al. | |
| 2012/0134024 A1 * | 5/2012 | Lander | C03C 15/00 |
| | | | 359/599 |
| 2012/0138997 A1 | 6/2012 | Tasaki et al. | |
| 2012/0276317 A1 * | 11/2012 | Tse | C09J 11/08 |
| | | | 428/40.2 |
| 2013/0317175 A1 * | 11/2013 | Guo | C08F 265/06 |
| | | | 525/185 |
| 2013/0323468 A1 * | 12/2013 | Myers | C03C 17/007 |
| | | | 428/143 |
| 2015/0168604 A1 * | 6/2015 | Guo | B29D 11/00798 |
| | | | 252/582 |

\* cited by examiner

OPTICAL LIGHT DIFFUSER AND METHOD FOR MEASUREMENT THEREOF

This application claims benefit, under U.S.C. § 119 or § 365 of PCT Application Number PCT/US2013/062068, filed Sep. 27, 2013, and U.S. Provisional Application No. 61/708,216, filed Oct. 1, 2012, said applications incorporated herein by reference.

FIELD OF THE INVENTION

The invention relates to optical light diffusers for use with point light sources, such as LED lighting. The optical diffusers achieve an optimum balance of light transmission and hiding power. The optical light diffuser is a transparent plastic matrix having organic particles dispersed within the matrix. The particles are crosslinked beads having specific particle sizes and loading. Different beads can be combined to provide added properties such as a textured surface, and to optimize hiding power and light transmission. The invention also relates to a luminous device containing at least one light-emitting diode and a cover made of the optical light diffuser. The invention further relates to a method for assessing hiding power.

BACKGROUND OF THE INVENTION

Polymer particles are used in a polymer matrix to manage light diffusion. For example, U.S. Pat. No. 7,547,736 describes the use of particles having an average particle size of 15 to 70 microns to provide a frosted look and textured surface, and U.S. Pat. No. 8,163,827 describes a high light transmission diffusion screen having inorganic pigments and refractive index-matched particles.

Point light sources create a visible shape of the light source, and there is often a desire to hide the light source shape, creating a more diffuse lighting. As used herein, "point light source" means any shaped source of electromagnetic radiation in the 4,000-7,700 Angstrom range. This includes, but is not limited to, incandescent, fluorescent, neon, argon and LED light sources.

Light emitting diodes (LEDs) are being increasingly favored as a light source, since they use far less electricity and produce less heat than standard incandescent or fluorescent light bulbs. LEDs provide a very bright, point light source, yet the output (7000° K) often appears harsh and causes an uncomfortable glare. This is a challenge for lighting designers, as many applications demand an illumination and low glare. Light devices that integrate one or more LEDs include, for example, motor vehicle illumination devices (at the front or rear), indicating panels, luminous displays, spotlights, street lighting, box-letters, etc.

These luminous devices consist of a light source and a cover (also called a lens or a diffuser) made of a plastic whose function is to mask and protect the light source, while still ensuring good transmission of the light emitted by the light source. The plastic may be colored or may have decorative elements or patterns. The cover also has the function of scattering the emitted light so that the illumination is softened and not dazzling. The scattering of the light emitted by the light source is achieved by dispersing scattering particles of organic or mineral nature in the plastic.

Replacing a conventional light source with an LED results in a modification of the illumination. This is because an LED, especially an LED having a high luminous flux, exhibits directional illumination, whereas, for example the illumination of a neon tube is from 0 to 360°. In addition, the emission spectrum of an LED is completely different from that of a conventional light source.

WO 2006/100126 describes a thermoplastic cover with dispersed beads for use with LEDs to form luminous devices. 3-30% of scattering particles are dispersed in a transparent plastic. The particles can be inorganic or organic and have mean diameters of from 0.5 to 100 microns. There is no description of combinations of particle size and loading, and no teaching of hiding power.

The addition of scattering particles helps to soften the effect of the LED light source, but the scattering also reduces light transmission. Some LED lighting cover manufacturers add pigments, such as $BaSO_4$, to the cover to increase the hiding power, though this can dramatically decrease the light transmission.

The hiding power of an LED covering is generally measured by the industry in a qualitative manner. A quantitative haze measurement is sometimes used as a surrogate, but it does not adequately correlate to the hiding power.

Applicant has now found that an optical light diffuser can be formed using a transparent plastic matrix having dispersed therein particles having specific particle sizes, and particle loading, to maximize both the light transmission and LED hiding power. Additionally, a test has been developed to quantitatively measure the hiding power for an LED covering. The optical light diffuser can be combined with one or more LED light sources to provide a luminous device.

SUMMARY OF THE INVENTION

The invention relates to a cover for a point light source having a composition comprising a transparent plastic matrix having dispersed therein from 0 to 10 equivalent loading weight percent of small diffusing particles having a mean particle size of from 2 to 20 microns, and from 0 to 25 equivalent loading percent by weight of large diffusing particles having a mean particle size of from 30 to 80 microns, where the total weight percent of diffusing particles is from 3 to 30 equivalent loading weight percent, the weight percent based on the polymer matrix, and wherein the optical transmission is greater than 75 percent and the hiding power is greater than 40 percent.

The invention further relates to a synergistic blend of from 1 to 10 weight percent of small diffusing particles, and from 2 to 10 weight percent of large particles.

The invention further relates to a luminous device having at least one point light source, and the cover of the invention.

The invention still further relates to a method for measuring the hiding power of an LED cover, comprising the steps of:

a) forming plaque of the material to be tested at uniform thickness—for example 2 mm thickness;

b) measure the optical transmission of the sample on a Perkin Elmer Lambda 950 at 0 inches from the integrating sphere, and 560 nm;

c) measure the optical transmission of the sample on a Perkin Elmer Lambda 950 at 2 inches from the integrating sphere, and 560 nm;

d) calculate percent hiding power as a percentage, as the difference between the two transmission measurements (0 inch and 2 inch), divided by the 0 inch transmission measurement, times 100 to obtain a percent hiding power.

DETAILED DESCRIPTION OF THE INVENTION

Figure 1:
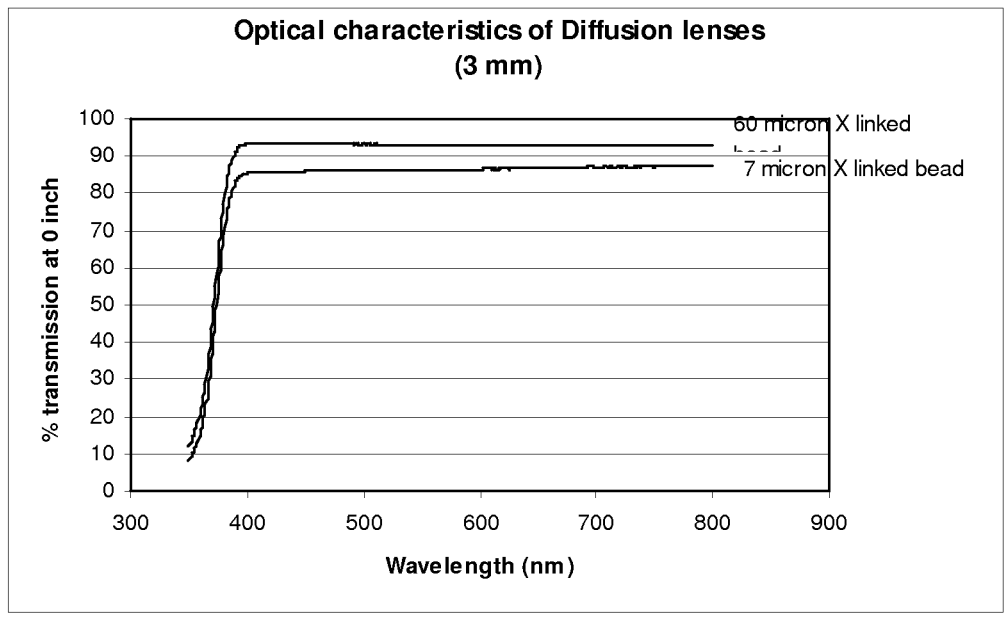
FIGS. 1 and 2: Compare the transmission curves as a function of the distance from the integrating sphere on a Perkin Elmer Lambda 950.

The invention relates to optical diffusers for point light sources having a transparent plastic matrix in which diffusing particles of specified particle sizes and particle loadings are dispersed. This provides a balance of high light transmission and high hiding power. The invention also relates to a method for quantitatively measuring the hiding power for an LED light source.

As used herein, unless otherwise described, molecular weight shall mean weight average molecular weight, and percent shall mean weight percent.

The particle loading level within the thermoplastic matrix will be described herein as an equivalent loading level. By "equivalent loading level" is meant the weight percent of particles found in a cross-section of a 2.0 mm thick sample. For example a 10% equivalent loading on a 2.0 mm thick sample would mean there are 10% by weight particles and 90% by weight thermoplastic matrix. One of skill in the art would understand that the diffusion and transmission properties of a composition depend on both the thickness of the sample, and the weight percent of particles in the composition. A sample having half the loading weight percent of particles, but being twice as thick, would have the same equivalent loading level. The use of an equivalent loading level does not limit the invention to only a 2 mm thickness—but is meant to standardize the loading ranges over the thicknesses covered in this invention.

Transparent Plastic

The term "transparent plastic" denotes a thermoplastic or thermosetting polymeric material, having a light transmission in the visible range of at least 50%, preferably at least 70% and even more preferably at least 80% according to the DIN 67-507 standard (this is the light transmission of the transparent plastic with no scattering particle). Useful transparent plastics include, but are not limited to, crystal polystyrene; polyethylene terephthalate (PET); a transparent, especially clarified, polyolefin, for example clarified polypropylene; acrylics; a transparent polyamide; styrene acrylonitrile (SAN) and polycarbonate.

Acrylics, polystyrene, styrene acrylonitrile and polycarbonate are the preferred transparent plastics due to their ease of processing, commercial availability and high transparency. In addition, these two plastics exhibit excellent thermomechanical strength, allowing compact luminous devices to be produced. In the case of compact luminous devices, heat builds up and rapidly raises the temperature inside the device. While the energy efficiency of an LED (i.e. the efficiency of converting electrical energy into light energy) is much better than for an incandescent lamp, some of the energy is nevertheless converted into heat.

Acrylic polymers, as used herein, are meant to include polymers, and copolymers having two or more different monomer units that are formed from alkyl methacrylate and alkyl acrylate monomers, and mixtures thereof. The alkyl methacrylate monomer is preferably methyl methacrylate, which may make up from greater than 50 to 100 percent of the monomer mixture. 0 to less than 50 percent of other acrylate and methacrylate monomers or other ethylenically unsaturated monomers, included but not limited to, styrene, alpha methyl styrene, acrylonitrile, and crosslinkers at low levels may also be present in the monomer mixture. Suitable acrylate and methacrylate comonomers include, but are not limited to, methyl acrylate, ethyl acrylate and ethyl methacrylate, butyl acrylate and butyl methacrylate, iso-octyl methacrylate and iso-octyl acrylate, lauryl acrylate and lauryl methacrylate, stearyl acrylate and stearyl methacrylate, isobornyl acrylate and isobornyl methacrylate, methoxy ethyl acrylate and methoxy methacrylate, 2-ethoxy ethyl acrylate and 2-ethoxy ethyl methacrylate, and dimethylamino ethyl acrylate and dimethylamino ethyl methacrylate monomers. (Meth) acrylic acids such as methacrylic acid and acrylic acid can be useful for the monomer mixture. Most preferably the acrylic polymer is a copolymer having 70-99.5 weight percent and more preferably 80 to 99 percent of methyl methacrylate units and from 0.5 to 30 weight percent of one or more $C_{1-8}$ straight or branched alkyl acrylate units.

The acrylic polymer can be an alloy with one or more compatible polymers. Preferred alloys are PMMA/polyvinylidene fluoride (PVDF) alloys, and PMMA/polylactic acid (PLA) alloys The alloy contains 2 to 95 weight percent, preferably 5 to 90 weight percent, and more preferably 20-80 weight percent of the PMMA homopolymer or copolymer, and 5 to 98 weight percent, preferably 10 to 95 weight percent and more preferably 20 to 80 weight percent of the compatible polymer.

The transparent polymer matrix may contain additives, including impact modifiers, and other additives typically present in polymer formulations, including but not limited to, stabilizers, plasticizers, fillers, coloring agents, pigments, dyes, antioxidants, antistatic agents, surfactants, toner, refractive index matching additives, additives with specific light diffraction, light absorbing, or light reflection characteristics, and dispersing aids. In one embodiment, an additive is provided to help prevent degradation of the composition upon exposure to radiation, such as high levels of UV radiation or gamma radiation. Useful radiation stabilizers include, but are not limited to poly(ethylene glycol), poly (propylene glycol), butyl lactate, and carboxylic acids such as lactic acid, oxalic acid, acetic acid, or a mixture thereof.

Useful impact modifiers include block copolymers, graft copolymers, and core/shell impact modifiers. The impact modifier may be present at a level of from 0 to 80 weight percent, preferably 5 to 45, and more preferably from 10 to 30 weight percent, based on the total layer of matrix polymer and all additives. The level of impact modifier can be adjusted to meet the toughness needs for the end use of the composition. Core-shell impact modifiers are multi-stage, sequentially-produced polymer having a core/shell particle structure of at least two layers. Preferentially, the core-shell modifier comprises three layers made of a hard core layer, one or more intermediate elastomeric layers, and a hard shell layer.

Particles

The diffusing particles of the invention have a mean particle size of either from 2 to 20 microns, preferably from 3 to 15 microns, and more preferably from 5 to 10 microns, or from 30 to 80 microns, preferably from 40 to 70 microns, and more preferably from 50-65 microns. Any particle size distribution can be used, though the particle size distribution is preferably relatively narrow, with 90 percent of the particles being within +/−50% of the mean particle size. There is a general trend that large beads provide good light transmission but poorer hiding power, while the smaller beads provide good hiding power but reduced transmission. A higher loading of particles generally provides an increase in hiding power, with a corresponding reduction in light transmission.

The particles can be of any shape. Particles formed from suspension or emulsion synthesis are relatively spherical. Particles formed from the grinding of cast sheet will be irregular. In one embodiment particles are formed from the grinding of cast sheet and have irregular shapes. The irregular shape can aid in light dispersion.

When a frosted or rough is desired, large particles having a mean particle size in the range of from 30 to 80 microns, preferably from 40 to 70 microns, and more preferably 50-65 microns can be used to provide an optimum balance of transmission, hiding power and surface roughness.

When a smooth surface is desired, such as, for example a medical use, it has been found that that small particles having a mean particle size of from 2 to 20 microns, preferably 3 to 15 microns, and more preferably from 5 to 10 microns, at an equivalent loading of from 6 to 10 weight percent, and preferably about 8 weight percent, based on the total weight of the matrix polymer plus beads, provides a transmission of greater than 85% and a hiding power of greater than 85%.

In one embodiment, it was surprisingly found that when a portion of the larger beads (30 to 80 microns, preferably from 40 to 70 microns, and more preferably 50-65 microns) were replaced by a portion of smaller beads (2-20 microns, preferably 3 to 15 microns and more preferably 5 to 10 microns), a synergism occurred where the hiding power increased significantly without a noticeable change in the light transmission. The equivalent loading level of the smaller beads is from 1 to 10 weight percent, preferably from 2 to 6 weight percent, and the equivalent loading level of the larger beads is from 2 to 10 weight percent, and preferably from 4 to 6 weight percent. It is possible for the equivalent loading level of the smaller beads to be higher than the level of larger beads, for example a blend of 6-8 weight percent of the smaller beads with 3-5 weight percent of the larger beads.

The difference between the refractive indices (measured according to ASTM D 542) of the diffusing particles and of the transparent plastic should be greater than 0.01 and preferably between 0.015 and 1.

The diffusing particles maintain their shape and resist deformation under normal processing conditions of heat and pressure during incorporation into the polymer matrix and subsequent formation into articles. The particles can either be high Tg polymers, such as fluoropolymers or polyamides, or may be crosslinked polymer beads. Useful polymer particles of the invention include, but are not limited to, polyamide and copolyamide particles, styrene-based particles (comprising greater than 50 percent by weight styrene monomer units), silicone particles, polytetrafluoroethylene (PTFE) particles, polyvinylidene fluoride particles, and alkyl(meth)acrylate particles.

In one preferred embodiment, methyl methacrylate particles are used. These comprise greater than 50 weight percent, preferably greater than 70 weight percent, and more preferably greater than 80 weight percent methyl methacrylate units and 0.5 to 20 percent, preferably 1 to 10 percent, of a monomer possessing at least two C=C double bonds acting as crosslinking agent. This may for example be 1,4-butanediol di(meth)acrylate, ethylene glycol di(meth) acrylate, tetraethylene glycol di(meth)acrylate, propylene glycol di(meth)acrylate, pentaerythritol tetra(meth)acrylate, allyl methacrylate or divinylbenzene. In another embodiment, acrylic copolymers containing a majority of butyl acrylate are used.

The crosslinked polymer based on methyl methacrylate or other alkyl(meth)acrylates advantageously includes from 0 to 20% of a comonomer having at least one ethylenic unsaturation copolymerizable with methyl methacrylate, chosen from styrene, alpha-methylstyrene, acrylonitrile, a $C_1$-$C_{10}$ alkyl(meth)acrylate, such as for example methyl acrylate, ethyl (meth)acrylate, butyl (meth)acrylate, benzyl (meth)acrylate, 2-hydroxyethyl (meth)acrylate and phenyl (meth)acrylate. Styrene, α-methylstyrene, benzyl methacrylate and phenyl methacrylate are monomers of choice for modifying the refractive index of the methyl-methacrylate-based particles.

Useful methyl-methacrylate-based scattering particles are advantageously prepared by polymerization in a dispersed medium, such as suspension polymerization and emulsion polymerization, according to a recipe given for example in the document EP 1 022 115, US 2002/0123565 or US 2002/0123563. The methyl-methacrylate-based scattering particles are substantially spherical. The mean diameter is determined by parameters known to those skilled in the art, such as for example the stirring speed or the amount of suspension agent. Particles may also be formed by the grinding of a cast methyl-methacrylate sheet, creating irregular shaped particles.

Mineral particles (pigment) may also be added at low levels. It is known in the art to add pigment to increase the hiding power of a composition, however the pigment also reduces the transmission, and therefore the use of pigment is not preferred.

Surface Roughness

In many applications, there is a desire to have a relatively pronounced surface roughness (producing what is often called a "frosted" effect). Surface roughness also reduces the visual effect of scratching and marring. Surface roughness may be obtained in several ways. In the case of a cast sheet, the glass mold, which forms the sheet, may have a surface roughness that has been obtained by treating the glass of the mold, for example with hydrofluoric acid. Sandblasting may be used. A textured roller may be used with extruded sheet. The particles in the composition can also produce surface roughness, as the particles partially protrude from the surface—especially as the thermoplastic matrix cools and recedes. Particles having a mean particle size of from 30 to 80 microns and preferably 40 to 65 microns can produce a desired surface roughness. The surface roughness, denoted by Ra, is expressed in microns and can be measured using a roughness meter (for example of the Talysurf Surtronic 3P brand from Rank-Taylor-Hobson) according to the ISO 4287 and ISO 4288 standards. A surface roughness of between 0.5 and 4 µm, preferably between 1 and 3 µm on at least one of the faces of the cover allows the light-scattering effect of the scattering particles to be enhanced. The faces of the cover according to the invention may also be perfectly smooth and not have any pronounced roughness. In this case, the value of the surface roughness Ra is less than 400 nm, advantageously less than 300 nm and preferably less than 100 nm.

Method for Forming Coverings and Devices

There are several methods known to those skilled in the art for producing the diffusion covering of the invention. The diffusing particles and optional other particles and additives (dye(s), impact modifier, UV stabilizer, antioxidant, etc.) are mixed with the transparent plastic by means of an extruder or any other mixing tool suitable for thermoplastics as known to those skilled in the art. Recovered at the exit of the extruder are granules that are then formed to the desired shape using a conversion technique for thermoplastics, for example injection molding or compression molding. It is also possible to adapt the extruder in order to produce a sheet. This sheet is then formed to the desired shape after cutting and/or thermoforming.

The cover may have a variety of different geometries, depending on the nature of the intended application. For example, it may be in the form of a flat, curved or domed sheet, whether rectangular or circular, in the form of a disc, etc. It may also take the form of a letter of the alphabet or of any other sign or symbol in the case of an illuminated sign.

The cover generally has a thickness of between 0.001 and 15 cm, preferably between 0.01 and 10 cm, more preferably between 0.05 and 7 cm, more preferably between 0.1 and 5 cm and even more preferably between 0.2 and 4 cm. A thin film could be used as a covering, such as in a flexible film structure hanging below a point light source as a room lighting, for example as a curved film. Thicker covers may be injection molded, or thermoformed into a variety of shapes. One of ordinary skill in the art can imagine many ways to form the cover composition of the invention into a useful diffusion covering.

Uses

The composition of the invention is used as a covering for a point light source. The light source plus cover forms a luminous device. The cover may be a single layer, or may be a multi-layer structure. The cover is separated from the light source by a distance of between 0.11 and 50 cm, preferably between 1 and 40 cm, preferably between 2 and 20 cm and even more preferably between 3 and 20 cm.

The luminous device according to the invention has a variety of applications such as, for example:
- interior lighting (living room lamps, office lamps, etc.);
- advertising displays;
- illuminated signs (in this case, the cover may especially have the form of a letter, a number, a symbol or any other sign); and
- automobile lighting (for example the luminous device may be a headlamp, a daytime light, a direction indicator, a stop light, a fog lamp, reversing light, etc.).

Quantitative Hiding Power Test

Hiding power is somewhat related to haze, yet for many samples haze does not correlate well to hiding power. In general, the lighting industry relies on qualitative tests that vary from manufacturer to manufacturer, such as by ASTM 1003. In a commercial extruded lens or cover (2 mm thickness) the hiding power should be greater than 40% and preferably 50%, and not more than 95%. Below 40% the point light source such as an LED is visible as a pinpoint of light at a reasonable distance (2 inch). Above 95% and the percent transmission of the lens is compromised, lowering the lumens per watt. In the thinner lens 0.9 mm (injection molded) the hiding power should also be greater than 40%

Figure 2:
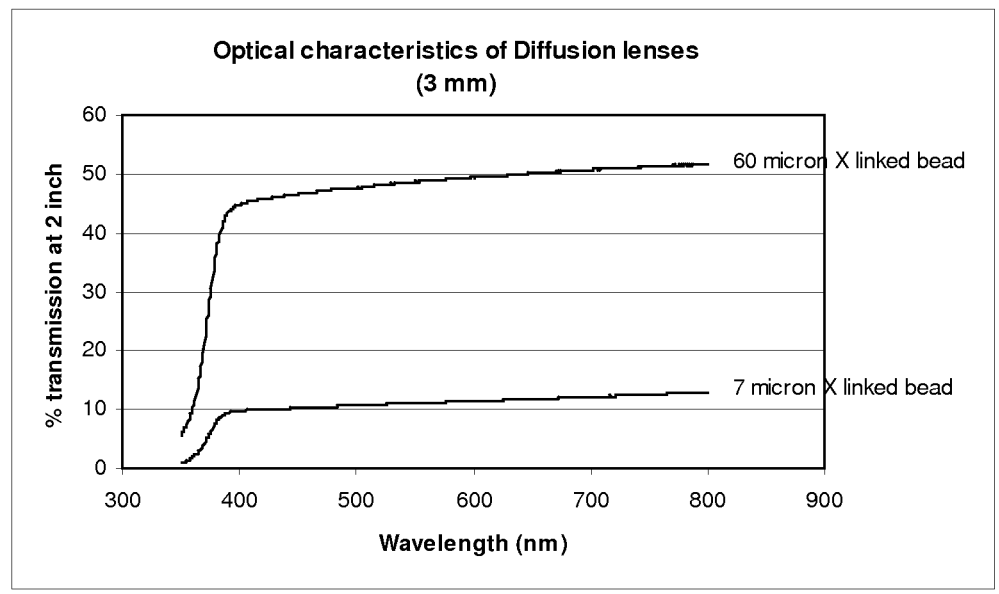

It has been found that the transmission curves are a function of the distance from the integrating sphere on a Perkin Elmer Lambda 950. Yet the change in the light transmission as a result of the distance from the integrating sphere is not constant for different materials, as can be seen in FIGS. 1 and 2 below. In the FIG. 1, the measurement was taken at 0 inches from (directly against) the integrating sphere). In FIG. 2, a two inch extension was added to the instrument, and the measurement taken on a sample two inches from the integrating sphere—so light diffused by the sample does not enter into the collector. As can be seen in the figures, the changes in % transmission are dramatic, and better represent the hiding power of the samples.

Calculation of hiding power as a function of distance from integrating sphere.

TABLE 1

| | % bead | distance from integrating sphere | | hiding power |
| --- | --- | --- | --- | --- |
| | | 0 inch | 2 inch | |
| 60 micron x-linked | 3.9 | 92.6 | 57.9 | 37.5% |
| 60 micron x-linked | 4.5 | 92.8 | 48.8 | 47.4% |
| 7 micron x-linked | 8 | 86.3 | 11.1 | 87.1% |

This observation has lead to the following method for obtaining a quantitative method for measuring the hiding power of a sample:

First a 2 inch by 2 inch square, 2 mm in thickness is extruded for each composition. The sample is placed in a Perkin Elmer Lambda 950 at 0 inches from the integrating sphere, and the transmission at 560 nm is measured. The sample is then moved to 2 inches from the integrating sphere, and the transmission at 560 nm is again measured. The hiding power is then calculated as the difference between the two transmission measurements (0 inch and 2 inch), divided by the 0 inch transmission measurement, times 100 to obtain a percent hiding power.

EXAMPLES

Particle size was measured using a NICOMP 380 DSL. A dilute sample of the beads was prepared by adding water to a small beaker containing the beads until the sample is only slightly cloudy or turbid. The sample is then injected into the instrument. Volume weighting values are reported.

Example 1

Figure 3:
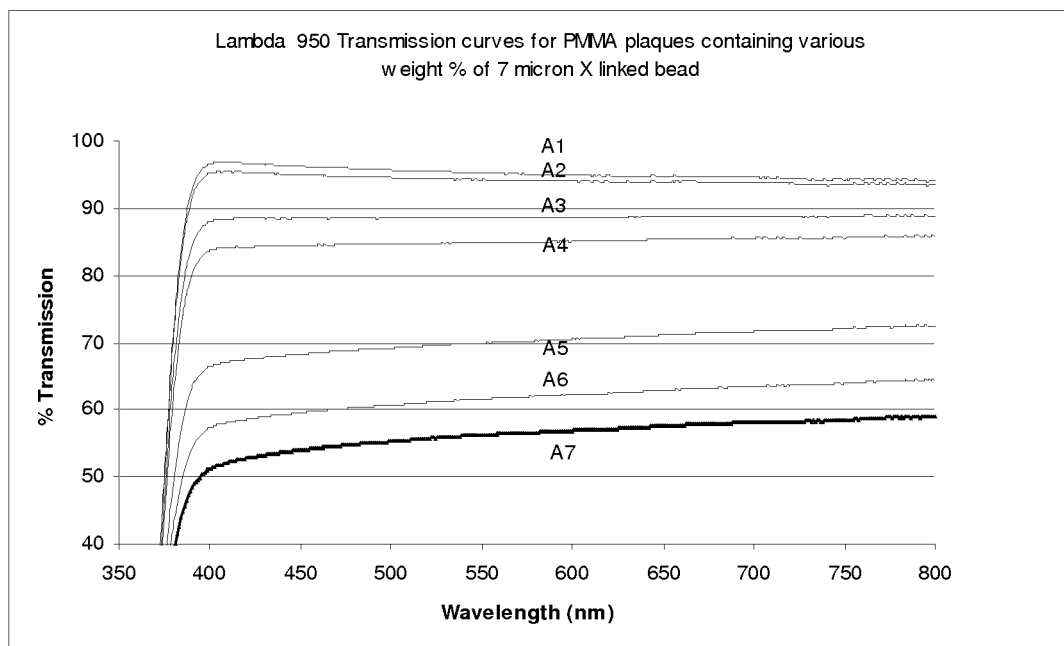
FIG. 3: compare the loading level of crosslinked beads to the transmission.

As seen in FIG. 3 and Table 2 below, a higher loading level results in a reduction in transmission, while a lower loading reduces the hiding power.

TABLE 2

Optical characteristics of PMMA plaques containing crosslinked acrylic-styrene beads having a mean particle size of 7 microns

| | A1 | A2 | A3 | A4 | A5 | A6 | A7 |
| --- | --- | --- | --- | --- | --- | --- | --- |
| % bead (wt/wt) | 2 | 4 | 6 | 8 | 10 | 20 | 40 |
| % transmission Lambda 950 at 560 nm | 95.2 | 94.2 | 88.5 | 84.9 | 70.1 | 61.7 | 56.4 |
| % transmission (Gardner Hazemeter) | 92.5 | 93.7 | 92.5 | 90.6 | 79.2 | 71.6 | 67.0 |
| % haze (Gardner Hazemeter) | 93.4 | 98.6 | 100.0 | 100.0 | 100.0 | 100.0 | 100.0 |

Example 2

The thermoplastic matrix material used in evaluating the optical properties of the composite plastic compositions was poly(methyl methacrylate) commercially available as PLEXIGLAS V920 or PLEXIGLAS V045 molding resin from Arkema Inc.

The crosslinked particulate polymer was extrusion blended with the thermoplastic PLEXIGLAS resin using a single or twin screw extruder at 250° C. (e.g. a 27 mm Leistriz extruder) with the thermoplastic material (pellets of approximately 3 to 6 mm in diameter and length.

The pelletized composite plastic compositions were then injection molded to a thickness of 0.035 mil (0.89 mm) using a 100 ton Engel injection molder at 250° C.

Optical measurements were made with a BYK Gardner hazz gard and a Perkin Elmer Lambda 950.

TABLE 3

| 7 micron bead | 60 micron bead | Thickness mm | % transmission 0 inch | % transmission 2 inch | Hiding power % | HP | Surface |
|---|---|---|---|---|---|---|---|
| 8 | 0 | 0.9 | 92 (measured) | 42 (measured) | 54 | excellent | smooth |
| 0 | 5 | 0.9 | 93 (calc) | 80 (calc) | 14 | poor | textured |
| 2 | 5 | 0.9 | 93 (measured) | 40 (measured) | 57 | excellent | textured |

As can be seen from Table 3, when a portion of the 60 micron beads is replaced by a portion of the 7 micron beads, a synergy occurs resulting in both a very high light transmission and a good hiding power.

What is claimed is:

1. A cover for a point light source having a composition comprising a transparent thermoplastic or thermoset plastic matrix having dispersed therein a blend of from 1 to 10 equivalent loading weight percent of small cross-linked diffusing particles having a mean particle size of from 2 to 20 microns, and from 2 to 10 equivalent loading percent by weight of large cross-linked diffusing particles having a mean particle size of from 40 to 80 microns, the weight percent based on the polymer matrix, and wherein the optical transmission is greater than 75 percent and the hiding power is greater than 40 percent, and wherein said cover has a surface roughness of from 0.5 to 4 microns.

2. The cover of claim 1, comprising from 6 to 10 weight percent of said small cross-linked diffusing particles and wherein said optical transmission is greater than 85% and said hiding power is greater than 85%.

3. The cover of claim 1, wherein said cover has a surface roughness of from 1 to 3 microns.

4. The cover of claim 1 wherein the diffusing cross-linked particles are a blend of 2 to 6 weight percent of said small cross-linked diffusing particles, and from 4 to 6 weight percent of large cross-linked diffusing particles.

5. The cover of claim 1, wherein said transparent polymer comprises a polymethyl methacrylate (PMMA) homopolymer or copolymer.

6. The cover of claim 1, wherein said cross-linked diffusing particles have a narrow particle size distribution, wherein 90 percent by weight of the particles are within 50% of the mean particle size.

7. The cover of claim 1, wherein the refractive index difference between the transparent polymer matrix and said cross-linked diffusing particles is between 0.015 and 1.

8. The cover of claim 1, wherein said transparent polymer matrix further comprises one or more additives selected from the group consisting of impact modifiers, and other additives typically present in polymer formulations, including but not limited to, stabilizers, plasticizers, fillers, coloring agents, pigments, dyes, antioxidants, antistatic agents, surfactants, toner, refractive index matching additives, additives with specific light diffraction, light absorbing, or light reflection characteristics, and dispersing aids.

9. The cover of claim 1, wherein said cross-linked particles are essentially spherical.

10. The cover of claim 1, wherein said cross-linked particles are irregular in shape.

11. A luminous device comprising at least one point light source, and said cover of claim 1.

12. The cover of claim 2, wherein said small cross-linked diffusing particles have a mean average of from 3 to 15 microns.

13. The cover of claim 1, wherein said transparent polymer is an alloy of PMMA with polylactic acid and/or polyvinylidene fluoride.

14. The luminous device of claim 9, wherein the point light source comprises one or more LEDs.

* * * * *